(12) United States Patent
Boschetti Sacco

(10) Patent No.: US 11,166,634 B2
(45) Date of Patent: Nov. 9, 2021

(54) SYSTEM FOR MONITORING PATIENTS SUFFERING FROM RESPIRATORY DISEASE COMPRISING A PORTABLE MEDICAL DEVICE AND METHOD BASED ON THE USE OF SUCH SYSTEM

(71) Applicant: MIR S.R.L.—MEDICAL INTERNATIONAL RESEARCH, Rome (IT)

(72) Inventor: Paolo Boschetti Sacco, Rome (IT)

(73) Assignee: MIR S.R.L.—MEDICAL INTERNATIONAL RESEARCH, Rome (IT)

(*) Notice: Subject to any disclaimer, the term of this patent is extended or adjusted under 35 U.S.C. 154(b) by 58 days.

(21) Appl. No.: 16/478,008

(22) PCT Filed: Nov. 16, 2018

(86) PCT No.: PCT/IB2018/059039
§ 371 (c)(1),
(2) Date: Jul. 15, 2019

(87) PCT Pub. No.: WO2019/102324
PCT Pub. Date: May 31, 2019

(65) Prior Publication Data
US 2019/0350466 A1    Nov. 21, 2019

(30) Foreign Application Priority Data
Nov. 21, 2017    (IT) .......................... 102017000133269

(51) Int. Cl.
*A61B 5/0205*    (2006.01)
*A61B 5/00*    (2006.01)
(Continued)

(52) U.S. Cl.
CPC ............ *A61B 5/0205* (2013.01); *A61B 5/002* (2013.01); *A61B 5/0022* (2013.01);
(Continued)

(58) Field of Classification Search
None
See application file for complete search history.

(56) References Cited

U.S. PATENT DOCUMENTS 7,267,636 B2 * 9/2007 Wang ..................... A63B 24/00
482/52
9,820,656 B2    11/2017 Olivier
(Continued)

FOREIGN PATENT DOCUMENTS

| EP | 3028627 A1 | 6/2016 |
|---|---|---|
| WO | 2017/087366 A1 | 5/2017 |
| WO | PCT/EP2017/076710 | * 4/2018 |

OTHER PUBLICATIONS

International Search Report and Written Opinion, dated Feb. 14, 2019, from corresponding PCT application No. PCT/IB2018/059039.

*Primary Examiner* — Brian T Gedeon
(74) *Attorney, Agent, or Firm* — Nixon & Vanderhye

(57) ABSTRACT

A system for monitoring the state of health of a patient suffering from respiratory disease including a portable medical device, the device including: a) a flow measurement device performing a spirometry measurement, and b) a reflecting photometric sensor performing an oxygen measurement or a measurement of blood oxygen saturation and heart rate. The system includes storage and comparison units in which a personalised plan of action for the patient is stored against which the spirometry and/or oxygen measurement data found are compared, displaying the result of such comparison on the display of a device connected to the internet so as to define the patient's state of health and
(Continued)

identify exacerbation of the disease on the basis of data obtained from both such spirometry and oxygen measurements. A method for monitoring the health of a patient suffering from respiratory disease implemented through the system indicated above is also claimed.

19 Claims, 11 Drawing Sheets

(51) Int. Cl.
    *A61B 5/1455*     (2006.01)
    *A61B 5/024*     (2006.01)
    *A61B 5/087*     (2006.01)
    *A61B 5/091*     (2006.01)

(52) U.S. Cl.
    CPC .......... *A61B 5/14552* (2013.01); *A61B 5/024* (2013.01); *A61B 5/087* (2013.01); *A61B 5/091* (2013.01)

(56) References Cited

U.S. PATENT DOCUMENTS

| | | |
|---|---|---|
| 2004/0039295 A1* | 2/2004 | Olbrich ................ A61B 5/0205 600/538 |
| 2010/0240982 A1 | 9/2010 | Westbrook et al. |
| 2013/0184540 A1* | 7/2013 | Boschetti Sacco .... G16H 40/40 600/301 |
| 2013/0310699 A1* | 11/2013 | Hart ................... A61B 5/04012 600/484 |
| 2014/0152673 A1* | 6/2014 | Lynn ....................... G06T 13/80 345/473 |
| 2015/0062078 A1* | 3/2015 | Christman ........... A61B 5/6826 345/174 |
| 2016/0235309 A1 | 8/2016 | Olivier |
| 2017/0189629 A1 | 7/2017 | Newberry |
| 2018/0140252 A1 | 5/2018 | Luxon et al. |
| 2018/0235480 A1 | 8/2018 | Olivier |
| 2019/0254534 A1* | 8/2019 | Koltowski ........... A61B 5/0205 |

* cited by examiner

SYSTEM FOR MONITORING PATIENTS SUFFERING FROM RESPIRATORY DISEASE COMPRISING A PORTABLE MEDICAL DEVICE AND METHOD BASED ON THE USE OF SUCH SYSTEM

BACKGROUND OF THE INVENTION

Field of the Invention

This invention relates to a system capable of detecting the state of health of a patient suffering from a respiratory disease through the use of a portable medical device. A method for monitoring such state of health of patients through using said system is also an object of the present invention.

Description of the Related Art

Alongside the widespread use of tablets and smartphones, digital technology is now redesigning the role of patients or people suffering from particular diseases; in fact such people see that they themselves can perform some "active" functions hitherto only available to the medical professionals.

However the rapid development of technology also makes it necessary for medical facilities providing care to alter their working methods to satisfy the requirements of citizens who through new "technological" devices can have information on their own health at any time and can therefore interact with such facilities in innovative ways.

The widespread use of smartphones and the growing development of wearable sensors support the implementation of new healthcare models focused on self-measurement and self-management to manage diseases, including continuity of care and emergencies. This also applies to patients with chronic diseases who are increasing their demand for "eHealth" technology of the self-care type.

These patients also include those suffering from respiratory diseases such as asthma, chronic obstructive pulmonary disease (COPD) and cystic fibrosis; these are common diseases which can significantly affect the quality of life of patients and their families.

Of these diseases, asthma is the most common.

Monitoring and cure of the abovementioned diseases is a real "global" problem, apart from being a substantial social and economic burden for health systems, as regards both monitoring and care during periods of wellness and the problem of frequent respiratory exacerbations requiring unscheduled medical visits or access to emergency departments.

Even more worrying, in recent years international organisations such as the WHO and GINA (Global Initiative for Asthma) have recorded a rapid increase in the number of patients with asthma in the world (an increase of 50% or more), with consequent high costs of direct or indirect treatment, to which must be added the social costs associated with patients' lost working and school days.

The guidelines for the treatment of asthma, specifically those relating to COPD, recommend that patients suffering from these diseases should receive a so-called "action plan" drafted by their own doctors. However, no-one can foresee when or how an acute exacerbation, that is an unforeseen and significant deterioration in the health of the respiratory tract, which may need urgent access to a hospital, will occur. It is known that so-called "action plans" are plans of initiatives, including treatment initiatives, prepared by doctors treating patients suffering from respiratory diseases.

Exacerbations are therefore associated with a significant health cost burden (specifically through the direct use of health organisations).

It follows that, from the point of view of both the patient's health and public burdens, prevention is an essential aim in the treatment of the main respiratory diseases. As evidence for the importance of this, it should not be forgotten that patients suffering from some respiratory diseases, such as for example COPD, present with frequent exacerbations and suffer more rapid decline of lung function, poorer quality of life, reduced physical activity and a higher rate of mortality.

At the present time, in order to confirm that an exacerbation is present experts concentrate their attention on symptoms, and in particular their severity, for example: symptoms not present or symptoms of mild, moderate or severe intensity. However, symptoms are subjective in that they depend on the patient's perception of them and they can also show variability from day to day.

Thus there is a real need for a medical device and method based on results obtained from it to provide objective confirmation of exacerbation and facilitate timely treatment.

US2010/0240982 describes systems and methods for assessing the quality of sleep in adults and children. This prior document describes a data acquisition unit worn on a patient's or user's forehead to collect physiological data during sleep. A nasal mask or nasal cannula is also provided in association with such data acquisition unit, all this also being associated with a headband surrounding the back of the patient's head to keep the whole system in position. Finally a top strap extends over the back of the patient's head, where it is connected to the headband to provide the system with further stability.

A strip of sensors may be associated with the headband so that they are held in position on the user's forehead. This strip may comprise disposable EEG (electro encephalogram) sensors and a reusable pulse metering sensor.

A signal associated with the flow of air which can be used to identify sleep disturbances such as apnoea is detected through the mask or nasal cannula. Such air flow data is obtained through a pressure transducer connected to said data acquisition unit located on the user's forehead.

This may also be connected to peripheral sensors such as EEG sensors, a finger pulse measuring device, sensors which measure movement of the legs, etc. All to determine the user's sleep architecture and/or to identify sleep disruption, which may have an adverse effect on quality of sleep.

A strip of sensors may also be incorporated into the band located on the patient's/user's forehead in order to detect physiological signals which may be used for measurements correlated with sleep architecture and sleep disruption made by the data acquisition unit. Among the sensors there is the possibility of using red or infrared light-emitting diodes and photodiodes in a reflection sensor which can be used to calculate haemoglobin oxygen saturation and the user's heartbeat, to obtain a photoplethysmographic signal that can be used to measure respiratory force through changes found in venous pressure in the forehead.

The United States text mentioned above therefore relates to a system which makes use of a device which as a result of its position and purpose can only be used when the patient is at rest. Use of such a system on a patient who is awake and in movement is wholly unthinkable. Such a system requires the user to be wholly passive or sleeping.

US2010/0240982 mentioned above therefore relates to a system for analysing the quality of sleep. The measuring device worn is only used to measure respiratory parameters which are completely different from those which are used in a spirometry test. In fact the purpose of detecting respiratory parameters in sleep is to identify disturbances in spontaneous respiration under resting conditions, such as for example hypoventilation and sleep apnoea (SA) caused by obstruction of the airways. This is because in sleep breathing is spontaneous and respiratory flow is reduced.

Conversely, a spirometry test requires the full cooperation of the patient, who must be perfectly conscious and must blow into a suitable device with the maximum velocity possible, performing all actions specified as dictated by a specific standard provided by the main world pneumological associations (ERS European Respiratory Society and ATS American Thoracic Society). For example, in spirometry the patient must first of all breathe in the maximum possible quantity of air and then breathe it out so that the peak flow (PEF) and the maximum volume which can be breathed out in the first second (FEV1) can be measured. Typically this result is obtained with the help of a doctor or a health worker who encourages the patient to blow at the maximum speed and with the greatest force possible. As an alternative, the patient is guided by encouraging software which through images helps him to achieve maximum respiratory performance so that the measured parameters are as similar as possible to normal, or better.

With regard to the measurement of respiratory parameters, this prior document relates to a system and a method which has no similarity with the devices and methods used in the field of spirometry: the only commonality between them is the use of a flow measuring device.

With regard to the measurement of oxygen parameters, this prior document uses a sensor of the reflecting type positioned on the forehead, used to determine any respiratory effort during sleep, as described.

Also, US2010/0240982 relates to exacerbations of diseases associated with sleep such as hypoventilation and obstructive apnoea (OSA). On the contrary, the aim of spirometry is to identify respiratory diseases such as asthma and bronchial obstruction whose diagnosis—according to the guidelines of the main pneumological associations—has nothing to do with sleep. For example, in the case of asthma, the bronchial inflammation which causes an obstruction of the airways cannot be detected during sleep, just as in the case of COPD an exacerbation which causes obstruction of the airways cannot be detected during sleep. Furthermore, to repeat, while sleep is studied under conditions of spontaneous respiration, spirometry requires a standard forced expiratory action to be performed in order that specific parameters such as PEF, FEV1, FVC, FEF25-75, etc., can be measured.

In conclusion, US2010/0240982 relates to systems and methods which cannot be used in spirometry tests, as well as systems which are difficult and inconvenient to apply.

US2013/0184540, in the name of this applicant, relates to an integrated system/device to monitor and report medical information for management based on data from patients with a chronic disturbance. This prior document describes a central unit which can separately receive a removable sensor to perform a spirometry measurement or, alternatively, a finger sensor to perform an oxygen measurement test, to measure the concentration of oxygen in blood and heart rate.

With this object the central unit is provided with a mechanical connection system to connect alternately to a connector connected to the removable sensor to perform the spirometry test or to another connector for the sensor to perform the oxygen measurement test.

Finally, the central unit has a contact display on one of its surfaces.

This prior document does not describe a device which incorporates within itself a spirometry sensor and a sensor to perform an oxygen measurement test, but a device which can alternatively and separately perform a spirometry test or an oxygen measurement test.

In addition to this, this known device uses a finger sensor which can be connected by wire to the central unit, which therefore represents a device which is in itself well defined and has its own dimensions which are added to those of the central unit.

This prior document therefore describes a device which is complex to use and which does not provide for the simultaneous performance of a spirometry test and an oxygen measurement test. The instrument described comprises three fundamental components: the control unit, a removable spirometry measuring device and a separate external unit for performing oxygen measurements. This external unit is provided with a cable which can be connected to the control unit through a connector. Such an instrument described in the prior document is not a "single" device, but a device in which the oxygen measurement sensor and that for the spirometry test are both incorporated into a single body.

US2013/0184540 uses a conventional removable sensor of the transmission type and no reference whatsoever is made in that text to fixed reflection sensors or reflecting photometric touch sensors.

For completeness we would point out that oxygen measurement devices of the "transmission" type use two signal emitters—red and infrared—facing the receiver and located within a specific sensor which generally comprises a rigid cap or a cap of flexible rubber similar to a finger or a spring clamp which has to be applied to the finger, the lobe of the ear, etc. By adjusting the compression exerted by the rigid cap or the spring clamp it is possible to avoid changing the vascularisation through excessive compression of the blood vessels at the site (for example a finger) where the measurement is being made. In conventional transmission oxygen measurement devices this possible alteration is also further controlled using measurement caps or spring clamps which are suitable for the dimensions of the finger (or earlobe) on which measurement of SpO2 is carried out. As a consequence there is a need to have caps or spring clamps of different sizes available (small, medium and large for use on children, adolescents and adults respectively), with a consequent increase in the number of usable devices.

This gives rise to a problem of the reliability with which oxygen and heart rate values are measured, especially in cases of self-measurement, and patients with little expertise not monitored by medical personnel are unable themselves to correct possible artefacts in the measurements brought about for example by changes in vascularisation through excessive compression of the blood vessels.

Furthermore, the device or system described in the prior document considered is of the "traditional" type provided with displays, keys and cables and operates with its own embedded software preloaded into the instrument. This results in the cost of the device being more than negligible.

EP3028627 describes a set of portable devices with the ability to measure temperatures of metabolic significance which are determined and communicated remotely. These devices are separate, but integrated, and can be integrated together and comprise a real time continuous measuring device capable of being placed in contact with user's skin, and a calibration unit comprising a hand-held calorimetric device with the ability to obtain the user's metabolic parameters such as CO2 output and the rate of O consumption.

This ability is achieved by analysing the composition of the air breathed in and/or breathed out by the user in a sampling chamber provided in such calibration unit.

The real time measuring device may be fixed to any part of the human body by means of a belt or tape; for example it may be attached to an arm, a user's chest or a leg. It uses an LED unit to illuminate the user's skin and the reflected light is detected by a detection module (one or more photodiodes or similar sensors) to determine a physiological parameter such as heart rate, respiration rate, haemoglobin concentration or oxygen saturation. This determination is made automatically.

This prior document does not describe a single device capable of determining a user's respiratory and physiological signals, but comprises two separate devices whose measurements can be used together. Thus the prior document in question describes a device or better an assembly of devices which when used by a patient or user is not very functional.

In addition to this, the calibration unit does not carry out a spirometry test with the characteristics indicated above and in accordance with very precise procedures, but calculates values for carbon dioxide and oxygen present in the air breathed in and/or out by the patient through measuring the composition of such air.

In addition to this, the calibration unit, in addition to O2, CO2, temperature and pressure sensors comprises surface electrodes for measuring a bioelectric impedance so that the device can be used to analyse respiration. The unit or device also comprises light sources and light detectors to measure heart rate.

Thus the prior document in question does not describe an integrated device which is capable of carrying out a spirometry test and an oxygen measurement test in just one operation.

US2017/0189629 describes a system for nebulising a medication during inhalation treatments. This prior document does not describe a system or device for carrying out a spirometry test. It includes a LED unit as part of an optical sensor based on photoplethysmography.

SUMMARY OF THE INVENTION

The object of the present invention is to provide a system which uses a single portable medical device which includes in itself the possibility of carrying out a spirometry test and/or an oxygen measurement test simply by holding the device in one hand, said system being capable of allowing patients suffering from respiratory diseases to be able to determine the condition of their own health in a simple and safe way.

Another object is that of providing such a system with an "integrated" device, that is one having the ability to carry out oxygen measurement and spirometry tests and which can be used to differentiate signs of exacerbation of the disease from changes in the daily symptoms which such a disease can cause, in an obvious and objective way.

Another object is that of providing a simple system which is easy to construct, is of low cost and in which the medical device is easy to carry and use by patients performing self-diagnosis of the condition of their health through the device, said use being capable of being carried out freely anywhere.

Another object is that of providing a system with a device capable of carrying out oxygen measurement and/or spirometry tests and which can display their results on a video or the display of a smartphone or computer in such a way that such data can also be monitored remotely by a doctor, who can then provide patients with instructions about immediate self-management of his disease, updated on the basis of the latest spirometry and oxygen measurements made.

Another object of the present invention is to provide a method for enabling patients suffering from a respiratory disease to have a clear situation of his own state of health through use of the abovementioned system which is capable of identifying exacerbations at the outset of their development with the object of facilitating timely access to treatment, the method being capable of being implemented anywhere.

These and other objects which will be apparent to those skilled in the art are accomplished by a system and a method capable of monitoring the state of health of patients.

BRIEF DESCRIPTION OF THE DRAWINGS

The following drawings are appended by way of a non-limiting example for a better understanding of the present invention, and in these.

DESCRIPTION OF THE PREFERRED EMBODIMENTS

Figure 1:
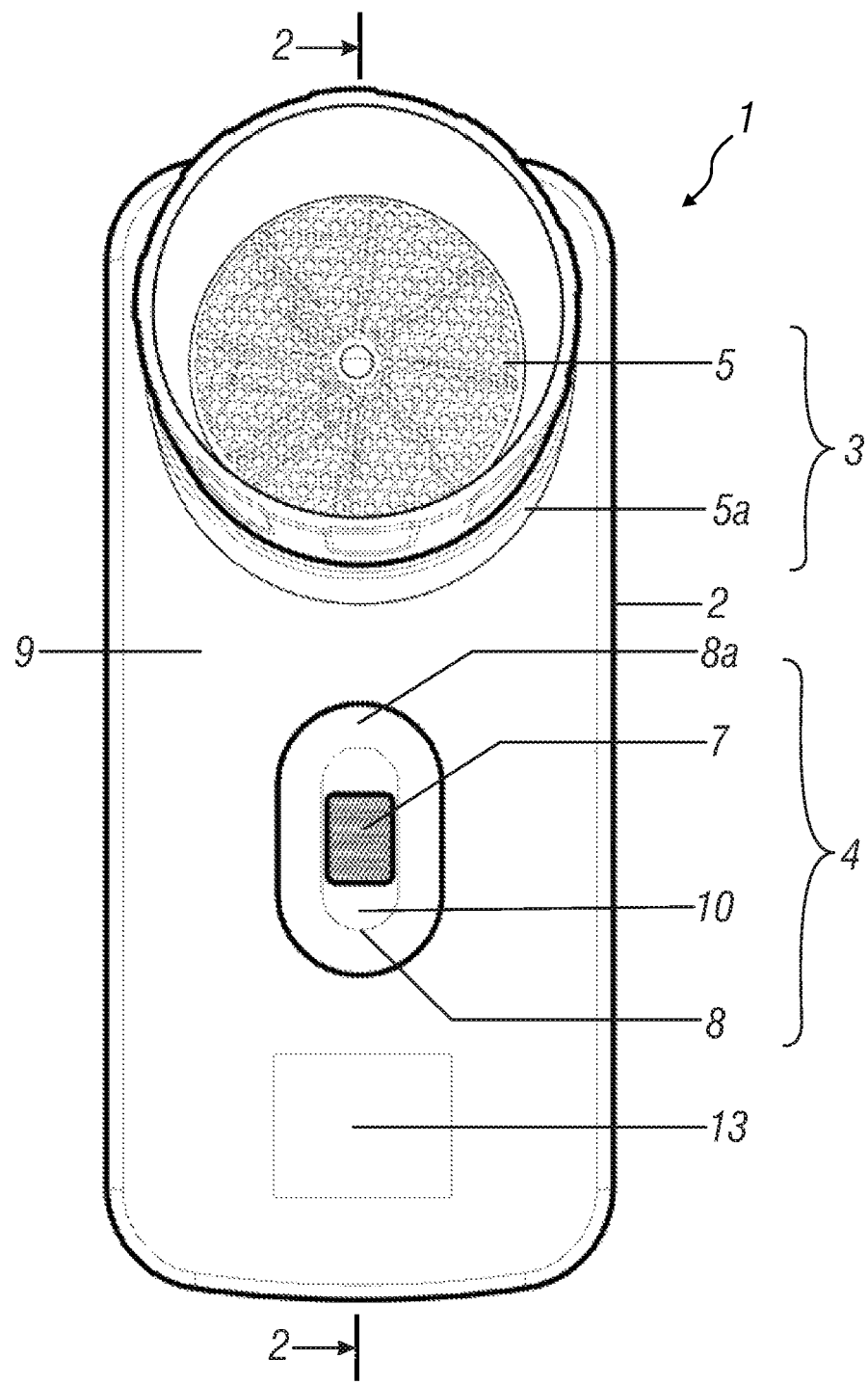
FIG. 1 shows a front view of a medical device for the system according to the invention.
Figure 2:
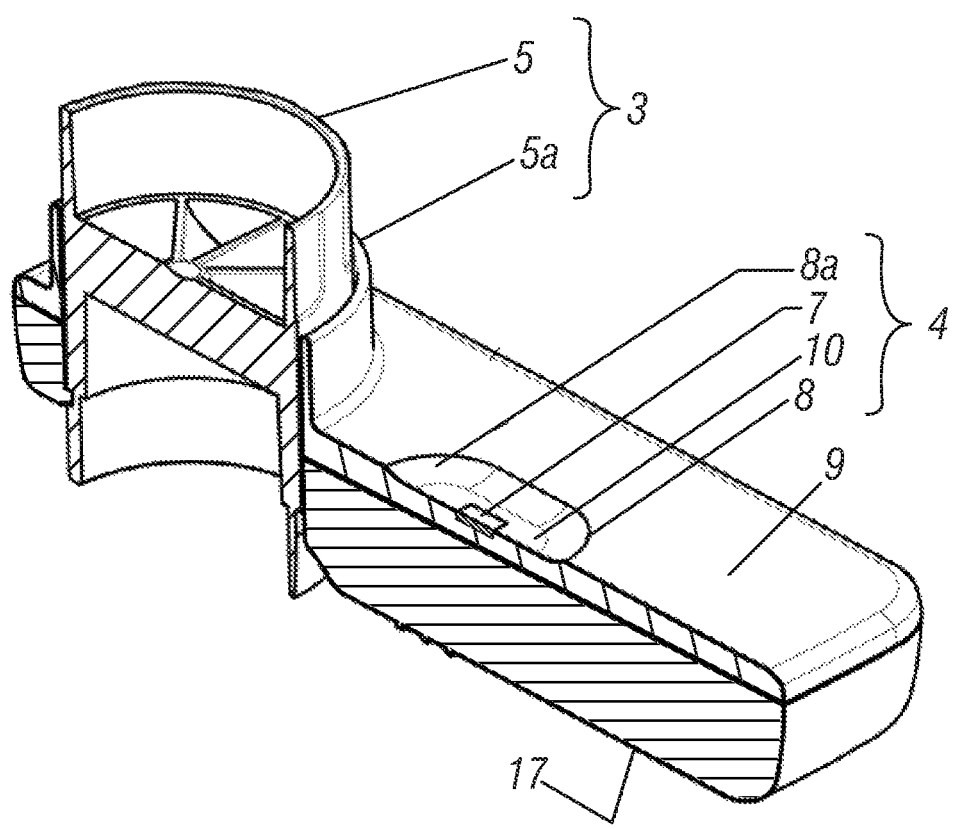
FIG. 2 shows a cross-section along the line 2-2 in FIG. 1 in perspective view.
Figure 3:
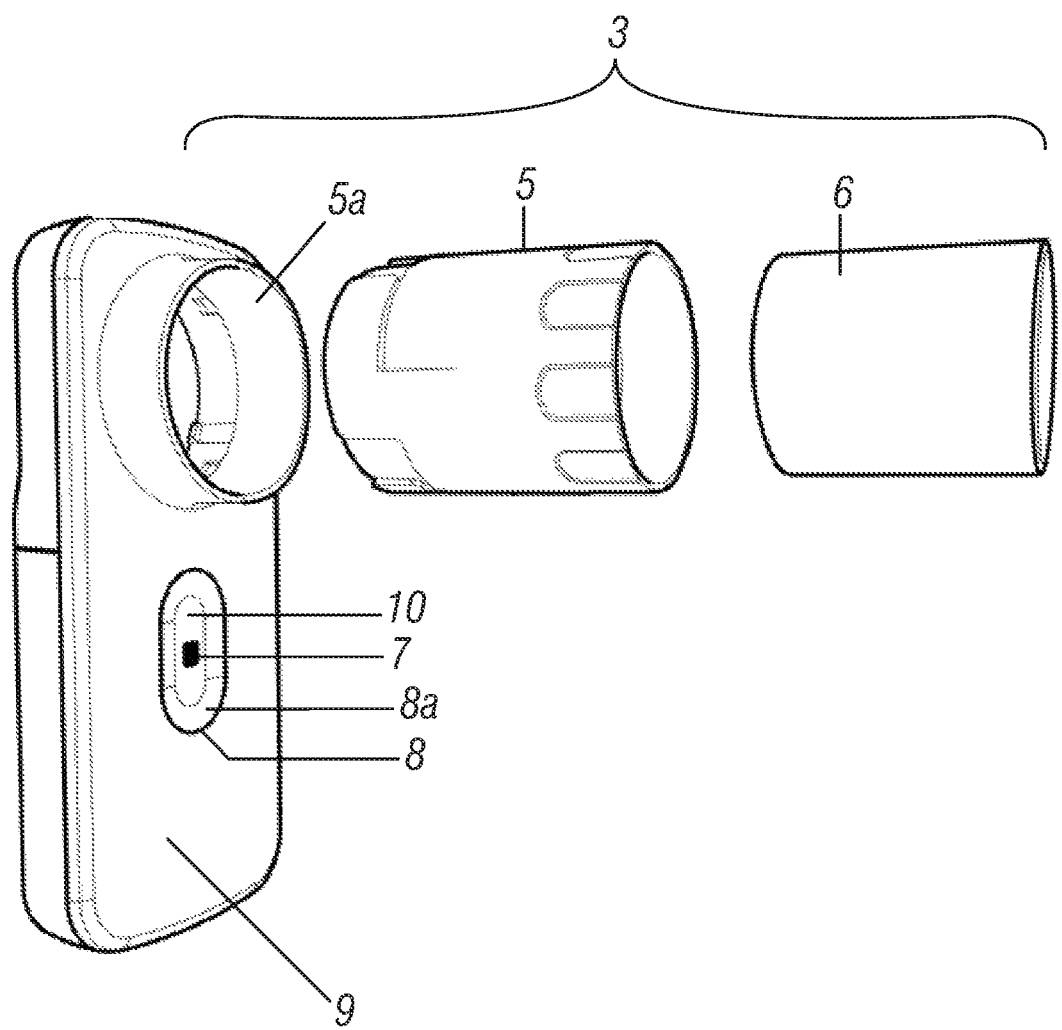
FIG. 3 shows the medical device for the system according to the invention in a partly exploded perspective view.

With reference to the figures mentioned, a medical device for the system according to the invention is generally indicated by 1 and comprises a body 2 with which are stably associated a component 3 (or flow measurement device) for carrying out a spirometry test and a component 4 for performing an oxygen measurement test comprising the measurement of $SPO_2$ (blood oxygen saturation) and heart rate. Component 3 in particular is defined by an element detecting respiratory flow 5a and the corresponding element sensitive to respiratory flow 5 (defined by a turbine caused to rotate by the air expelled forcefully by a patient performing a spirometry test) with which may be associated a tubular element 6 capable of acting as a mouthpiece for the patient. Component 4 on the other hand is defined by a reflecting photometric touch sensor 7 stably located in a suitable recessed seat 8 provided on one surface 9 of device 1; this seat is of elongated shape, substantially elliptical, and has a wall 8a which connects an internal or back part 10 of such seat (where it faces sensor 7) to wall or surface 9 of body 2 of device 1.

Typically, in order to calculate the SpO2 (which indicates the percentage of haemoglobin bound to oxygen present in arterial blood) the oxygen measuring device uses the emission of two different signal sources—having a wavelength in the red and infrared fields respectively—applied to the site bathed in the blood which is the object of measurement: for example the finger.

A photodetector is capable of measuring the absorption of each of the two signals from the haemoglobin: in fact a portion of the emitted signals is absorbed by the haemoglobin present at the site while another portion which is not absorbed reaches the photodetector.

The quantities of the signals—red and infrared—absorbed is proportional to the haemoglobin concentration, as a result of which, knowing the quantity of signals emitted, and measuring the quantity of signals reaching the detector, the percentage value of the main oxygen measurement parameter known as SpO2 can be calculated.

Because blood flow experiences changes due to heartbeats, by recording the changes in the signal captured by the photodetector it is also possible to calculate heart rate.

Oxygen measurement devices can be classified into two main categories: transmission and reflection types.

The transmission oxygen measurement device uses two signal emitters—red and infrared—located over the finger and a photodetector located under the finger. The three fundamental components are assembled within a specific sensor generally comprising a rigid cap or flexible rubber cap similar to a finger stall, or a spring clamp which is to be applied to the finger.

By adjusting the compression exerted by the rigid cap or the spring clamp it is possible to avoid changes in the vascularisation of the blood. This possible change is further controlled by using measurement caps or spring clamps which are appropriate for the size of the finger on which the SpO2 measurement is being carried out.

This however means that it is necessary to have available caps or spring clamps of different sizes—small, medium and large—for use on children, adolescents and adults respectively, with a consequent increase in the number of accessories.

The photometric touch sensor comprises a single integrated chip comprising all the components necessary for measuring oxygen. The chip in fact contains both the two side-by-side emitters (one at the red wavelength and the other in the infrared) as well as the photodetector.

It functions through reflection, in which the two signals generated by the emitters are directed towards the site used to measure oxygen, such as for example a finger. The blood circulating in the finger absorbs the two signals in different ways according to the haemoglobin present. In addition to this the signals undergo partial reflection which is captured by the photodetector.

By placing a finger on the top of the touch sensor the patient is able to obtain measurement of the signals linked to oxygen measurement.

In the case of transmission oxygen measurement—in addition to the advantages mentioned above—the reflection method is extremely compact in that it incorporates all the electronics processing the signals, including monitoring of the current in the individual emitters and the gain applied to the photodetector.

As a result of this it does not require a specific sensor, nor a rigid cap or a cap of flexible rubber, nor a spring clamp to be applied to the finger. In practice a single reflection sensor can be used without distinction by adults and children, wholly eliminating the need for different accessories as is otherwise required by the transition oxygen measurement device.

Figure 4:
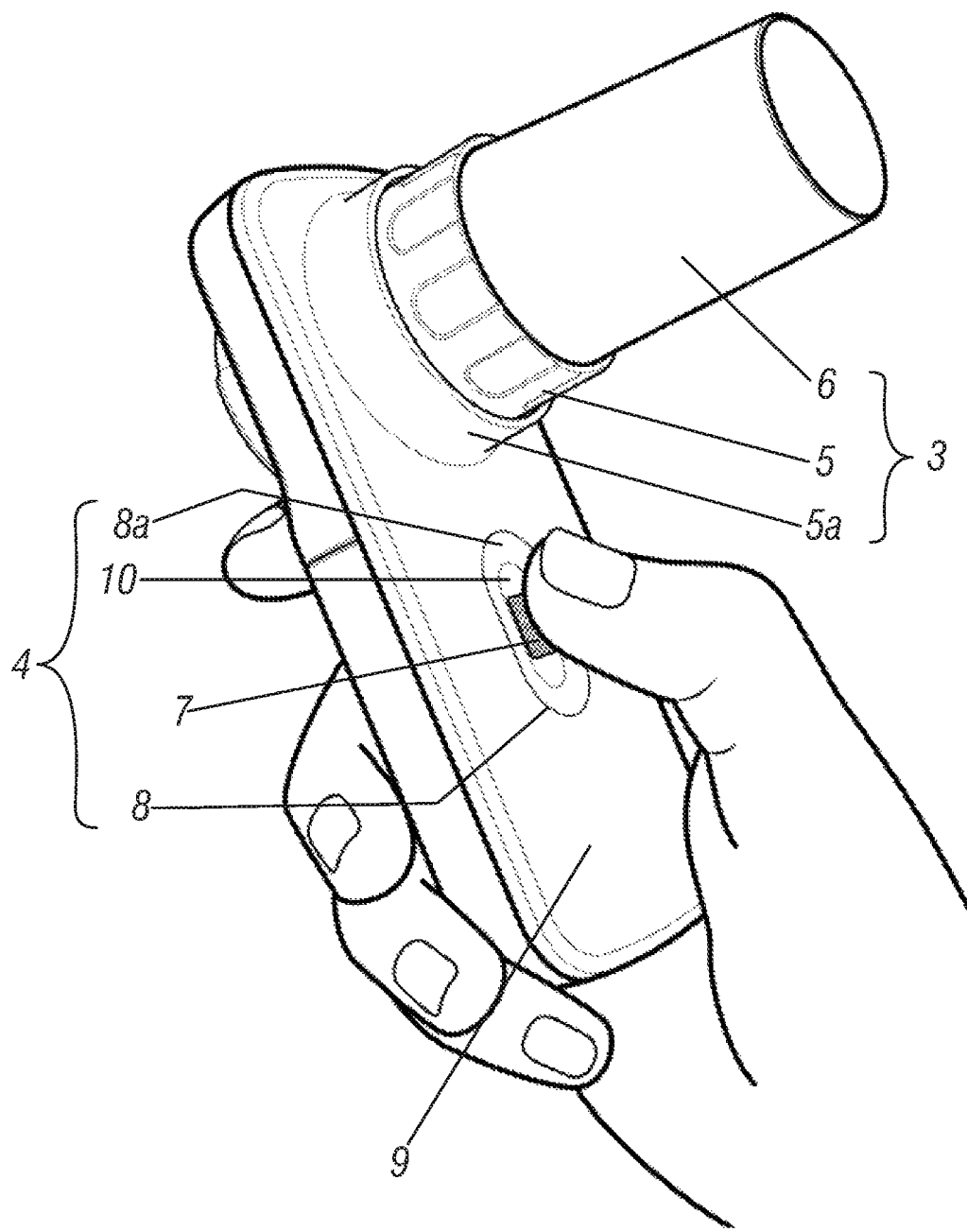
FIG. 4 shows the medical device for the system according to the invention in perspective view during use.

The shape of seat 8 is such that it can be adjusted to the anatomy of a patient's finger and allow component 4 to be used with patients of any kind, whether adults or children. By positioning a finger on the top of touch sensor 7 patients can obtain a reading of the signals linked to oxygen measurement; this as shown in FIG. 4. This detection may or may not be simultaneous with the spirometry test performed using component 3.

Sensitive component 4 is a single chip and is defined by a so-called "reflecting" sensor which requires a mere touch to measure $SpO_2$ (the main parameter for the measurement of oxygen). This is a radical innovation in comparison with the conventional array of "transmission" sensors hitherto available (with an emitter facing a receiver), in which a finger or an earlobe has to be inserted into a specific sensor connected to a medical device in order to be able to obtain the oxygen measurement.

On the contrary, using reflecting photometric technology, oxygen measurements can be performed simply by touching the sensor, without any other particular action.

This reflecting photometric technology does not require any specific applied sensor, so no adjustment to the patient's physical characteristics is required and the oxygen measurement device can be used without distinction by children, adolescents and adults. It also makes it suitable for use in the absence of medical personnel and it is therefore ideal for self-measurement and the self-management of health.

Within body 1 there is a control unit 13 capable of being connected to a portable device (such as a smartphone or tablet) or to an internet network present in the environment in which device 1 is located through a BLE (Bluetooth Low Energy) chip. In the latter case (the preferred solution) the connection is made through a network node, a gateway, a smartphone, a tablet or a fixed computer used as an access point for the network.

Control unit 13 comprises an incorporated microcontroller which simultaneously manages all the components of portable medical device 1 and which measures patients' spirometry and oxygen measurement parameters through components 3 and 4.

Device 1 is not provided with a visualiser or display and the data found by components 3 and 4 are sent for display on a computer, tablet or smartphone to which device 1 can be connected via control unit 13 (in addition to being capable of being "processed" by a suitable medical application executed on a web server, as will be indicated below).

Device 1 is therefore an element capable of detecting patients' spirometry and/or oxygen measurement data, but it is unable to display them directly (because it is not provided with a display). This device is a single unit with components 3 and 4 for carrying out the spirometry and oxygen measurement tests, components which cannot be separated from body 2.

In addition to this, these tests are also performed by holding body 2 in one hand, taking care to place a finger in seat 8 where the touch sensor is located.

The invention is a case of technological innovation characterised by a major discontinuity with the state of the art. As described, it comprises a portable device of small size (see FIG. 4 for comparison with a patient's hand), which is simple to use and convenient to manufacture and acquire. Device 1 detects the patient's data (through the spirometry and/or oxygen measurement tests) and works in combination with an innovative medical algorithm or application which can also be loaded onto a smartphone, a tablet, a computer or the like, which harmonises and integrates objective data (vital parameters measured by spirometry and oxygen measurement) and the patient's subjective data (symptoms). This application, constantly operating with storage means in which a plan of action for the patient is stored produces an objective indication of state of health and corresponding changes, and suggests to patients suffering from respiratory diseases what action they should take consistent with what is specified in the action plan (which in this case is digitised) provided and updated by their own doctors and capable of enabling the state of health of patients affected by respiratory disease to be monitored (as indicated above).

With its ease of use and portability anywhere and at any time medical device 1, together with the medical application and digitised action plan (provided by the doctor) enables anyone, even patients not used to serial programmed tests, to monitor their own state of health so that they can self-manage it more easily.

All patients will be able to check whether the perceived (subjective) worsening corresponds to a real (objective) change in clinical conditions envisaged in the digitised action plan provided by their own doctors and thanks to the immediate suggestions provided by the medical application patients will be able to adjust their treatment plans or, in extreme cases, go to emergency without uselessly losing time.

The system according to the invention (which comprises device 1, the medical application, the storage means and a portable device with a display such as a smartphone, tablet or computer) and the method correlated with it are therefore a pillar of tertiary prevention which is concerned with treating the disease experienced when it manifests itself clinically with symptoms and with preventing its progress and improving prognosis by reducing the risk of exacerbations. In addition to this, through its technical characteristics, this system also has a very specific part to play in secondary prevention programs intended to discover diseases such as asthma or COPD when they are at an asymptomatic stage, that is before they become clinically manifest, and therefore at the earliest possible stage. A classical example of secondary prevention is screening studies for the early diagnosis of respiratory diseases.

Finally, through its more general properties, that is the low cost of device 1, its simple use relating to widespread computerised facilities (for example smartphones), the potential for maximum penetration both as regards uses and number of users, the system according to the invention may become a tool in primary prevention for removing risk factors in healthy individuals (particularly in some categories of individuals at risk) to prevent the occurrence of diseases and maintain a good state of health. It is for example only necessary to think of primary prevention intended to stop tobacco smoking, which is well known to be the cause of respiratory diseases such as COPD.

The system making use of device 1, as mentioned, is mainly intended for patients suffering from respiratory diseases whose own doctors have determined a specific treatment action plan, and has properties which make it suitable for use by both children and adults. Because it enables patients to perform self-diagnosis of their own states of health (without needing the "physical" presence of medical personnel) the above-mentioned system also makes it possible to reduce health personnel, and thus to bring about significant economic savings from the point of view of public and private organisations caring for the abovementioned patients.

Through using device 1, the aforesaid system makes it possible to differentiate objectively between exacerbations and daily changes in symptoms which a patient presents or can present.

It is known that the collection and interpretation of accurate and objective data in significant quantities relating to the respiratory capacity of patients and blood oxygen saturation are a fundamental requirement for a valid clinical assessment. This requirement is satisfied by the present invention. In particular, the system according to the invention makes it possible to obtain an objective index—defined as the CEI (cardiorespiratory efficiency index)—which is useful for identifying exacerbations when they begin to develop, with the aim of facilitating timely access to treatment and avoiding exposing patients to an unnecessary or inappropriate treatment plan.

Distinguishing variations in symptoms from an exacerbation is challenging, but it is very important because correct and timely treatment of an exacerbation is certainly associated with rapid patient recovery.

As mentioned, in a preferred embodiment of the invention, device 1, through its low-energy-consumption BLE chip, communicates via the internet and interacts—through access points to the network such as gateways, smartphones, tablets, PC or any other hardware components provided with BLE technology and connected to the internet—with a medical application which can be run on comparison means such as a microprocessor unit (which may also be the microprocessor unit of the patient's computer or smartphone) or a web server (or in the cloud) which is in any event managed remotely by the treating physician; the application is also capable of monitoring device 1 so that the latter receives and executes commands and transmits digital data relating to the oxygen and spirometry measurements which it is capable of making, in real time. Device 1 uses a negligible quantity of energy (because there is no display and data is transferred to the network), and therefore a set of batteries is sufficient to perform thousands of tests. It is also known that Bluetooth communication, through the cryptography characteristic of such technology, ensures that sensitive medical data is protected.

The BLE communication system integrated in device 1 comprises the web-based application (mentioned above in the sense that it is connected to the device via the internet) to connect to and obtain data collected from that device and show patients their own plan of action (on the display of a tablet, computer or smartphone, as will be described below).

As is known, and as already described in the introductory part of the present document, for patients to have a treatment "action plan" is a fundamental part of the self-management of respiratory diseases, in particular as far as asthma is concerned.

When significant changes in the levels of intensity of symptoms and in values measured using spirometry and/or oxygen measurement techniques are encountered, a plan of action (written by the treating physician) includes all information on the actions which patients must take to reduce the symptoms and significantly reduce the risk of an exacerbation. This reduces the risks of emergency treatment and includes recommendations for actions which patients should undertake, including the use of medication.

Normally doctors are concerned to include some parameters which are useful for managing the disease in the action plan reference values and in the corresponding alarm thresholds. For example, the value of the envisaged peak flow (spirometry) and/or $SpO_2$ (oxygen measurement).

The plan of action also includes some symptoms of particular interest which patients must monitor in order to identify whether the respiratory disease is worsening, so as to obtain help very quickly and reduce the risk of an exacerbation.

Figure 9:
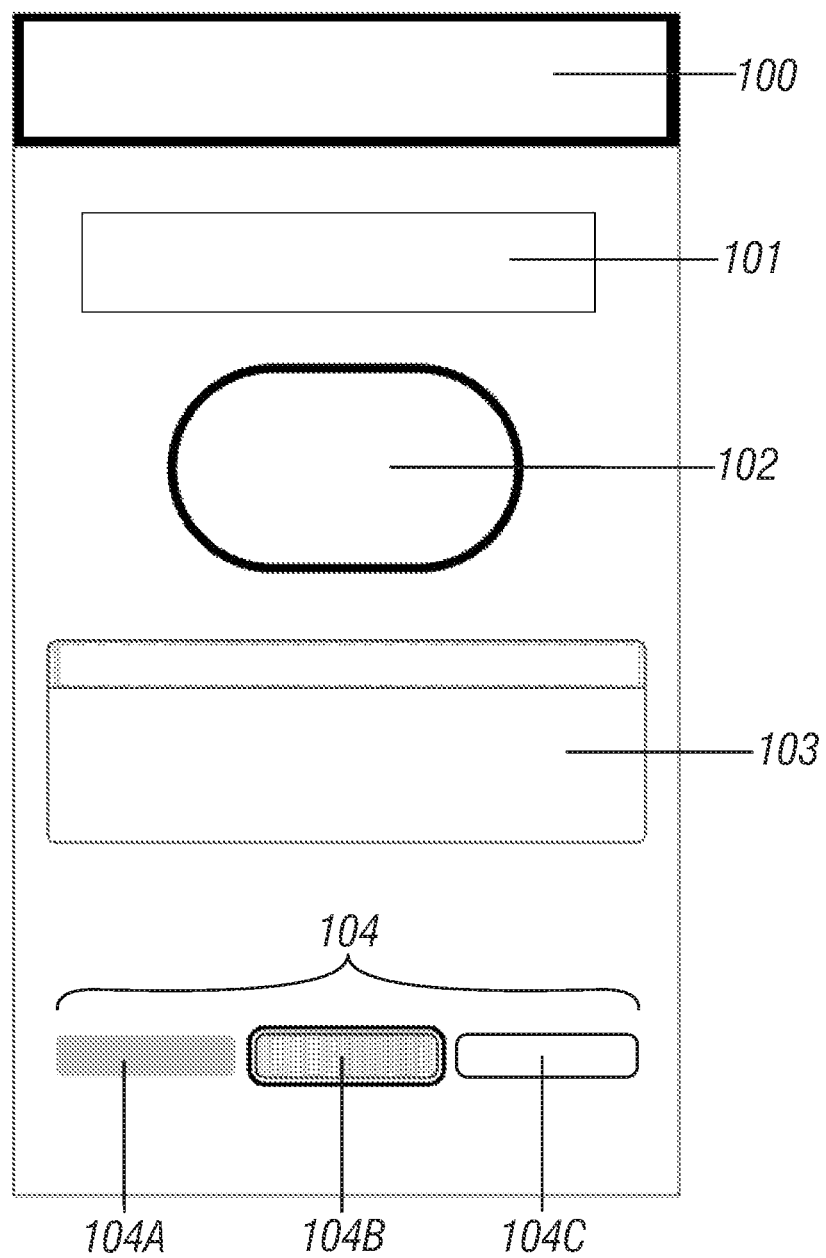
FIG. 9 shows a possible display of self-diagnosis results for a patient's status obtained through use of the device in FIG. 1.

In view of the fact that device 1 can be connected to a smartphone, tablet or computer, this plan of action is stored in storage means linked to the internet and managed by the treating physician who can introduce, update or modify the action plan for each individual patient. This action plan and consequent monitoring can be displayed (on one of such devices or on an attached screen) for example through a screen illustrated in FIG. 9. The screen illustrated here provides for various areas 100, 101, 102, 103 and 104 in which text relating to the measurement made by device 1 is displayed (area 101, for example no respiration), the severity of the data detected (area 102, for example "all well" or "severe"), written instructions relating to the health plan (area 103; for example "respiratory function is worsening" and/or "if the symptoms do not improve use the medication specified") and visual indications relating to the patient's status (area 104, for example advice is provided through coloured elements 104A, 104B and 104C if the patient is "well", if "the disease is worsening" or if "the situation is serious" respectively).

Area 100 simply indicates that what is shown in the other areas are the results of a check on the patient's situation.

When displayed, it corresponds to what is provided by the patient's action plan provided by the doctor.

As mentioned, device 1 can be used to measure oxygen and/or spirometry, and recent studies confirm that exacerbations are associated with changes in some physiological measurements. It will not be forgotten that oxygen measurement measures $SpO_2$ (blood oxygen saturation) and HR (heart rate), while spirometry measures various parameters including PEF (peak expiratory flow), FEV1 (forced expiratory volume in the first second), FVC (forced vital capacity), FEV25-75 (forced expiratory flow between 25% and 75% of FVC), etc.

Up to now, when prescribing self-management, doctors generally select only one of these spirometry parameters, generally PEV or FEV1. In the case of patients who have undergone lung transplants, on the other hand, the medical scientific literature suggests the use of FEV25-75.

Figure 6:
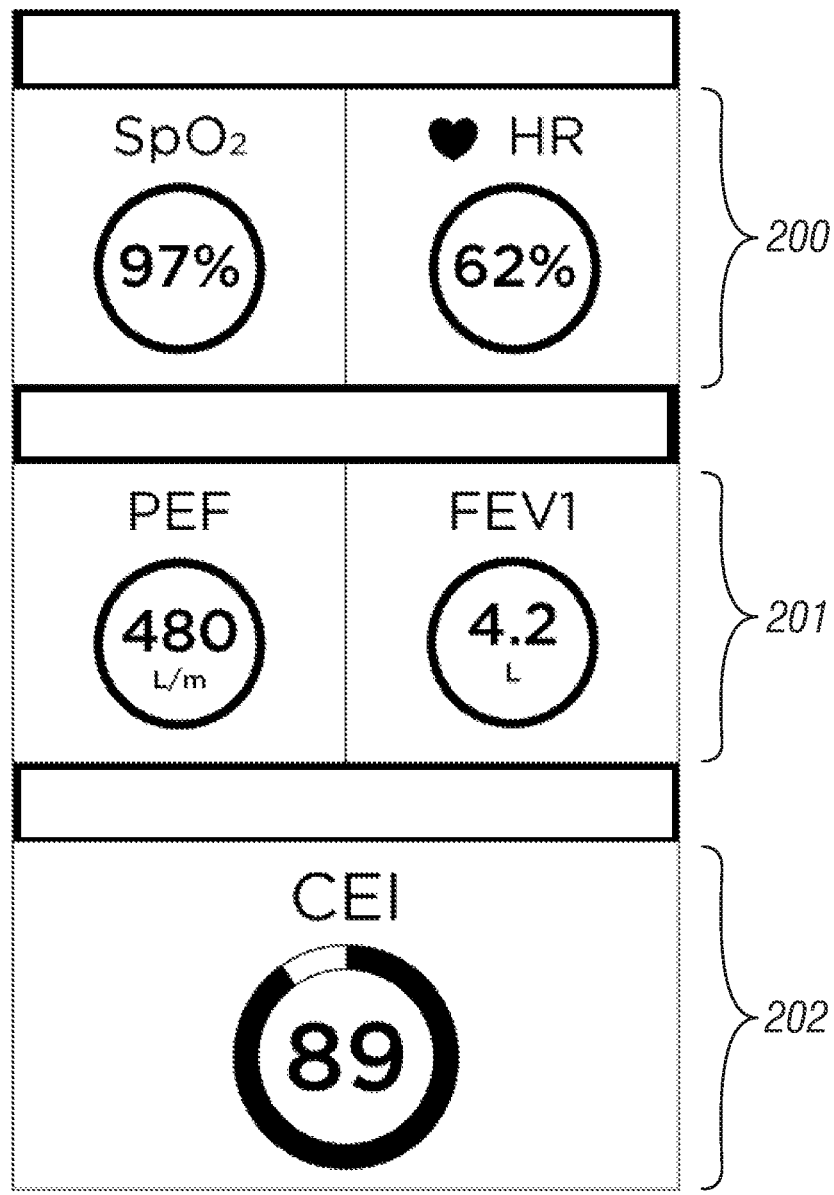
FIG. 6 shows a possible display of data associated with a patient through use of the device in FIG. 1.

The invention instead makes it possible to measure all the parameters listed above (FIG. 6) and to display them for example on the screen of a smartphone subdivided into various quadrants: 200 (for the oxygen measurement), 201 (for spirometry) and 202 (for the total value shown by the CEI index mentioned above).

The system according to the invention is therefore a solution for evidence-based (digital) health assistance, incorporated in real time, interactive, provided through a hand-held unit, which includes (inseparably) both component 4 defined by a touch sensor 7 to measure oxygen and component 3 to measure spirometry, all connected to a medical application installed on comparison means such as a remote internet server (managed by the treating doctor) or on a client which carries out the monitoring method according to the invention.

The medical application (or the algorithm permitting implementation of the aforesaid method) receives the parameters for the measurements made, processes them, compares them with corresponding reference values originating from storage in storage means, which are available and predefined (by the treating doctor in relation to the specific patient using the device) and generates data or a "score" relating to the patient's state of health, said data or "score" being capable of being read on a screen or displayed for example on a smartphone.

As a final result the application provides an objective index—known as the CEI (cardiorespiratory efficiency index)—of the patient's state of health and relative changes and recommends (or not) that actions should be undertaken in accordance with what has been specified by the digitised action plan provided by the treating doctor.

It is known that the comparison means and the storage means may be in the same device, such as an internet server or a patient's "client".

Figure 7:
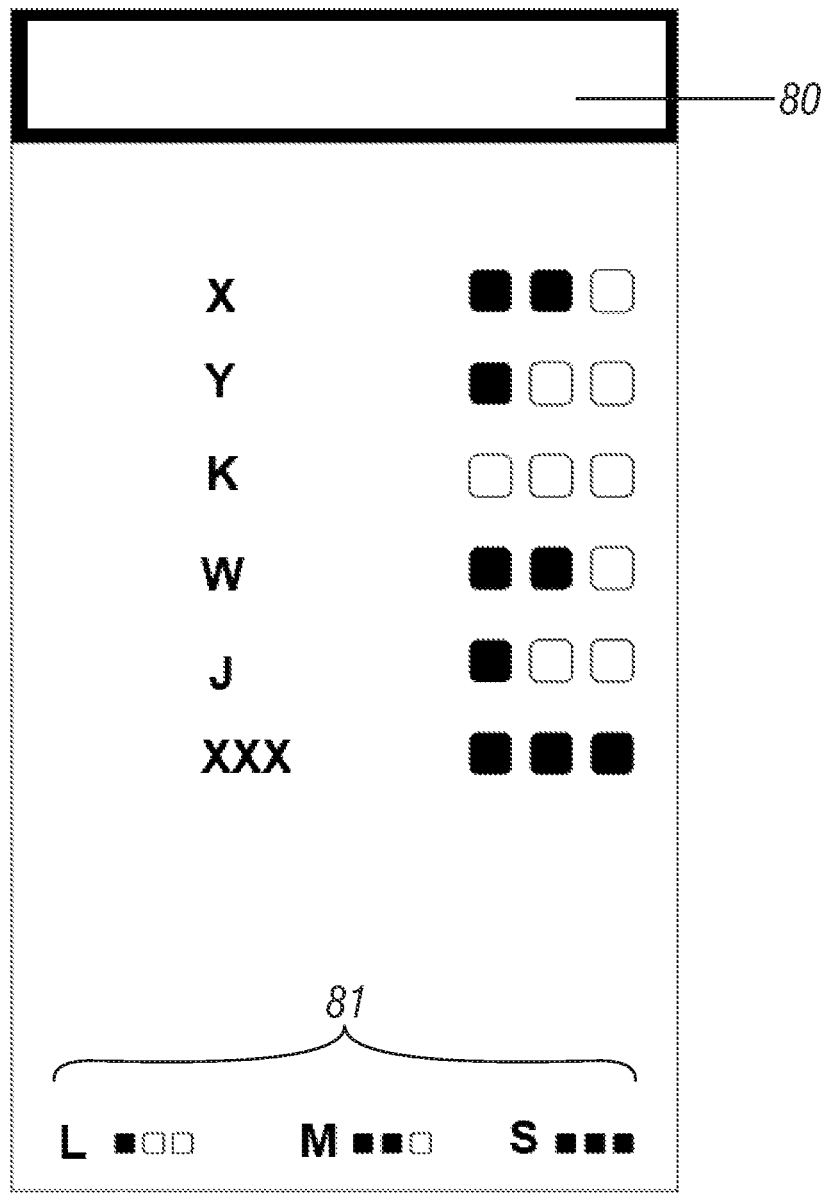
FIG. 7 shows another possible display of information obtained through use of the device in FIG. 1.

The medical application performs the CEI calculation which can be used to reach a decision relating to possible treatment or direct intervention on the patient by the doctor. In a few seconds all patients can make measurements of their "vital" parameters, the clinical results of which—together with the scores for symptoms (indicated by X, Y, K, W, J and XXX in FIG. 7, where the upper quadrant 80 indicates "insert the scores for symptoms" and the severity (mild (L), moderate (M) and severe (S) is indicated through legend (81) and the digitised action plan configured according to the needs of the situation—are automatically managed by the medical application which is for example resident on a remote internet server or client, with the value of a face-to-face visit to the treating physician himself.

It should be noted that the "score" given to a symptom corresponds to the feeling of "severity" which the patient experiences for that symptom.

Figure 8:
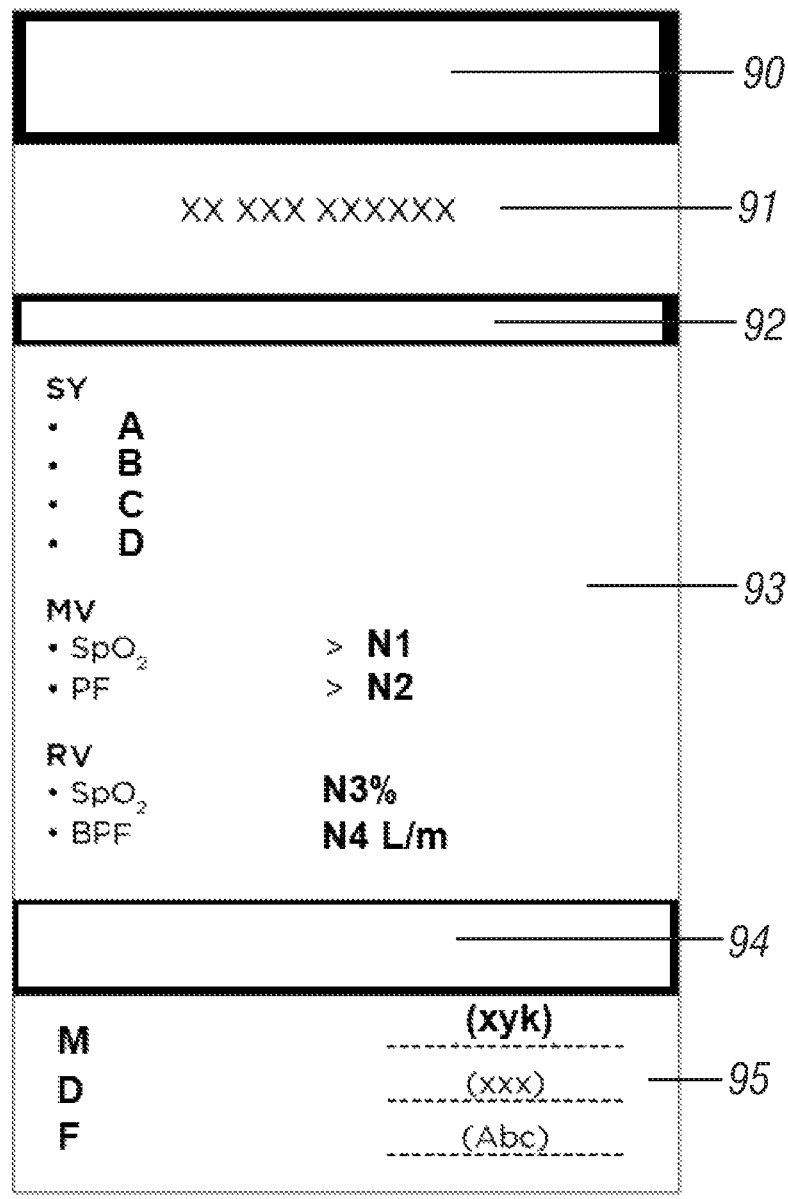
FIG. 8 shows a possible configuration of a plan of action provided by a doctor to a patient.

In addition to managing measurements made by the medical device and symptom scores, the medical application also uses the instructions of the digitised action plan shown in FIG. 8, comparing them with the abovementioned measurements.

As shown in that figure, the screen of the smartphone, tablet or computer shows for example: a first window 90 relating to the doctor's action plan; a second window 91 with doctor's data (and in particular his telephone number); a third window 92 relating to symptoms and measured values; a fourth window 93 relating to different symptoms SY (which through A, B, C, D for simplicity indicate the possible presence of coughing, chest pain, absence of breathing and shortness of breath), measured values (MV) of $SpO_2$ and peak flow (PEF peak expiratory flow) detected using the spirometry test, reference values (RV) of $SpO_2$ (BPF or best peak flow); a fifth window 94 relating to the treatment; and a sixth window 95 with the treatment prescription (drugs, doses, frequency of taking drugs indicated by M, D, F).

In this way the digitised action plan provides a number of advantages in comparison with the traditional written version:

it supports decisions for creating an evidence-based action plan;

it ensures greater accessibility and mobility 24 hours per day, 7 days per week;

it permits a standardised assessment in real time for monitoring diseases with interactive feedback on clinical actions;

it provides a reminder for automatic compliance with the treatment plan;

it improves efficacy and increases commitment from the patient, who capitalises on the moments of learning provided by the application;

it reduces the risk threshold due to irrational behaviour such as patients' "do-it-yourself" initiatives.

In situations where the client (smartphone, tablet, computer, etc.) uses an API (application programming interface) of the Bluetooth Web type, this can communicate directly with low-consumption Bluetooth devices directly through a web browser. In this way the abovementioned medical application can be installed in the server (or in the cloud) and reached by the medical device via the web (through connection with the smartphone or tablet, for example), so that it can operate on any type of client, regardless of the operating system installed (such as iOS, MacOS, Linux, Android, Windows).

In the case of "web" applications, these are easy for patients and doctors to reach; there is no need to install them on their own clients and they can be updated at any time to the benefit of all users accessing them.

Figure 5:
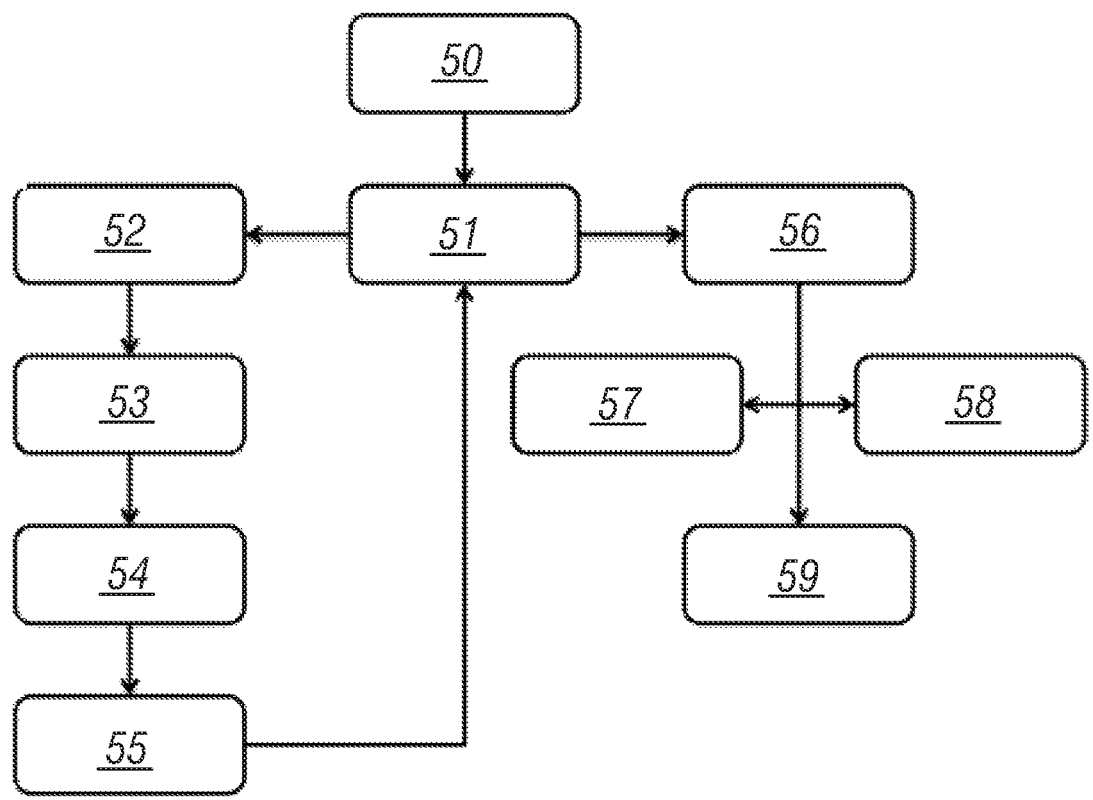
FIG. 5 shows a block diagram of a method for monitoring a patient's state of health performed through the device in FIG. 1.

Users can access the web application through a browser according to the procedure in FIG. 5. Once identified (block 50), users access an application which adapts its content to the specific requirement of their disease.

Through the browser the web application can provide advice of any kind—from a reminder to proceed with reading data to a reminder to take medication, to presenting the results of tests made using device 1 (block 51).

Through the use of Bluetooth, the web application communicates with the devices (block 52) and obtains spirometry and oxygen measurement data from them (block 53).

The application processes the CEI index (block 54) and allows the data obtained to be stored (block 55). In parallel it allows the system to be configured (block 56), subdivided into a configuration for calculating the CEI index (block 57), a configuration for the patient's action plan (block 58) and a configuration for the patient's data (block 59).

The web-based medical application can easily be replaced by an application run directly on a client—which may be the patient's smartphone or tablet—without the need for a browser or a nearby network or any other connection to the net.

For example, in the absence of an internet connection, the client application can manage the system, display the results of spirometry and oxygen measurements, request the entry of symptoms and the level of intensity perceived by a patient, process the CEI index, and directly interpret the results on the basis of a personalised configuration performed directly on the client in relation to the patient's requirement.

The above is another substantial difference between known solutions and the present invention. Starting from US2013/0184540, for example, the prior document describes a conventional medical tool provided with display, keys and cables and only and exclusively operates with its own embedded software which has been preloaded into the instrument. On the contrary, device 1 does not provide for a display, or cables or control keys, or switching-on keys and functioning is controlled via a smartphone on which a Mobile Medical App is installed or directly connected to a browser via Bluetooth Low Energy. This solution is particularly advantageous both through the enormous reduction in hardware costs and the possibility of using applications which can be easily downloaded from an on-line store, virtually infinitely extending the possibilities for use of the dedicated software which is not embedded in device 1. In this way, based on market offer, patients are in a position to select the applications which best meet their own needs. For example, in the case of asthmatic patients the relative application takes into account the action plan drafted by the doctor and parameters measured by the instrument and transmitted to the smartphone are used to establish the patient's state of health in relation to the action plan. It should be borne in mind that the action plan includes both therapeutic indications and the interpretation of measured parameters (spirometry and oxygen measurements) and the levels of symptoms (coughing, dyspnoea, chest constriction, etc.) to indicate the most appropriate treatment based on condition of health at that time. Use of the new tool enables doctors to change action plans remotely so that they can be made personalised and perfectly appropriate to patients' requirements and the typical variability of asthmatic disease.

In the case of other diseases—such as for example COPD or cystic fibrosis—the abovementioned application can provide incentivising images capable of stimulating patients when performing spirometry (through incentivising images on the smartphone) to help them achieve maximum respiratory performance so that the parameters measured are as far as possible similar to or better than the reference values. On the contrary, using the known solution in the prior document, the incentivising images cannot be displayed because when the instrument is held the display cannot be seen while the spirometry test is being performed.

The invention is therefore based on the fact that beyond the well-known scoring of symptoms, there are some tests such as oxygen measurements (which provide objective parameters such as $SpO_2$ and heart rate) and spirometry (which provides objective parameters on airway function such as PEF, FEV1, FVC, FEF25-75, etc.), assessment of which can reliably distinguish exacerbation from stable disease and/or daily variation in symptoms.

Use of device 1 automates the entire process described above and enables the system to provide an objective index of patients' conditions of health and corresponding changes in them, as well as suggesting to patients suffering from respiratory diseases what actions they should take to improve their condition in accordance with the digitised action plan provided by treating doctors, resident in the cloud and constantly managed by the doctors themselves.

By recording oxygen measurement and spirometry parameters together with variations in daily symptoms the invention is capable of distinguishing between normal variation in a symptom and an exacerbation, with acceptable sensitivity and specificity. This is through the CEI index, which objectively confirms exacerbations and is particularly suitable for patients suffering from respiratory diseases.

The index takes correctly recorded variations in data into account, both of the objective type such as the vital parameters of spirometry and oxygen measurement, as well as those of the subjective type such as symptoms commonly present in patients suffering from respiratory diseases (for example shortness of breath, coughing, chest pain, the production of catarrh, sore throat, etc.).

The CEI calculation requires data comprising both oxygen measurement and spirometry scores, symptom scores and reference data obtained from the digitised action plan which can influence patients' conditions of health. It will be noted that in this specific instance the term "score" indicates the degree of worsening or improvement of oxygen measurement and spirometry parameters and symptoms.

Figure 10:
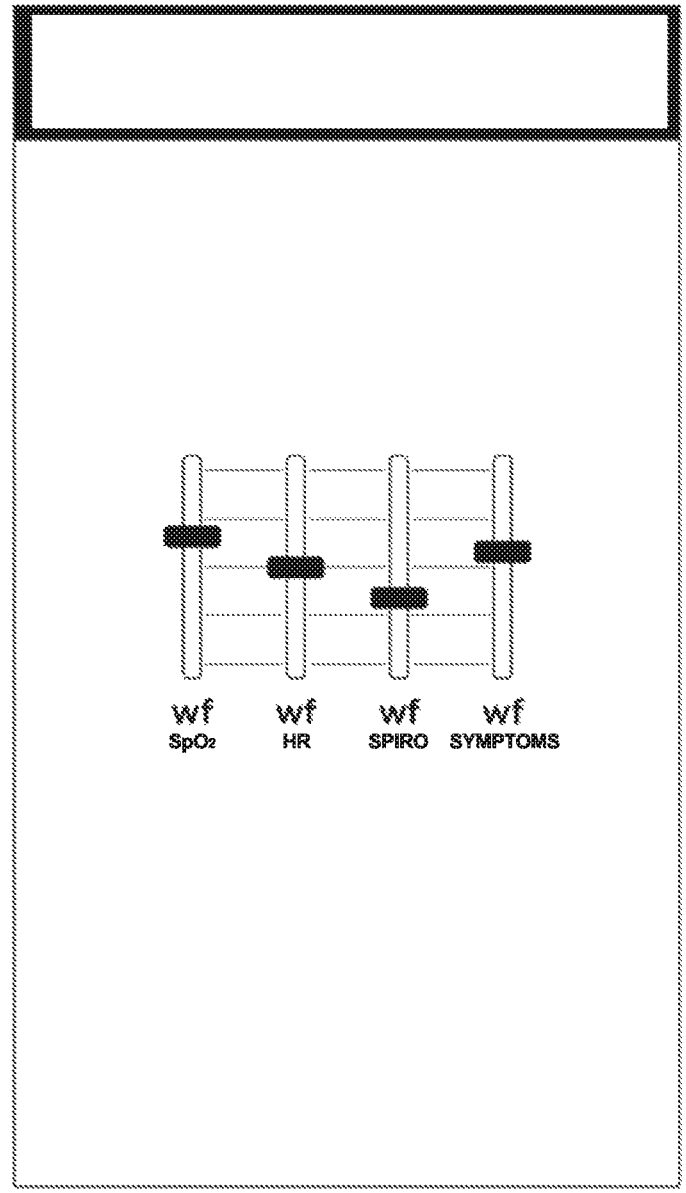
FIGS. 10 and 11 show possible screens for ways of setting up the device in FIG. 1.
Figure 11:
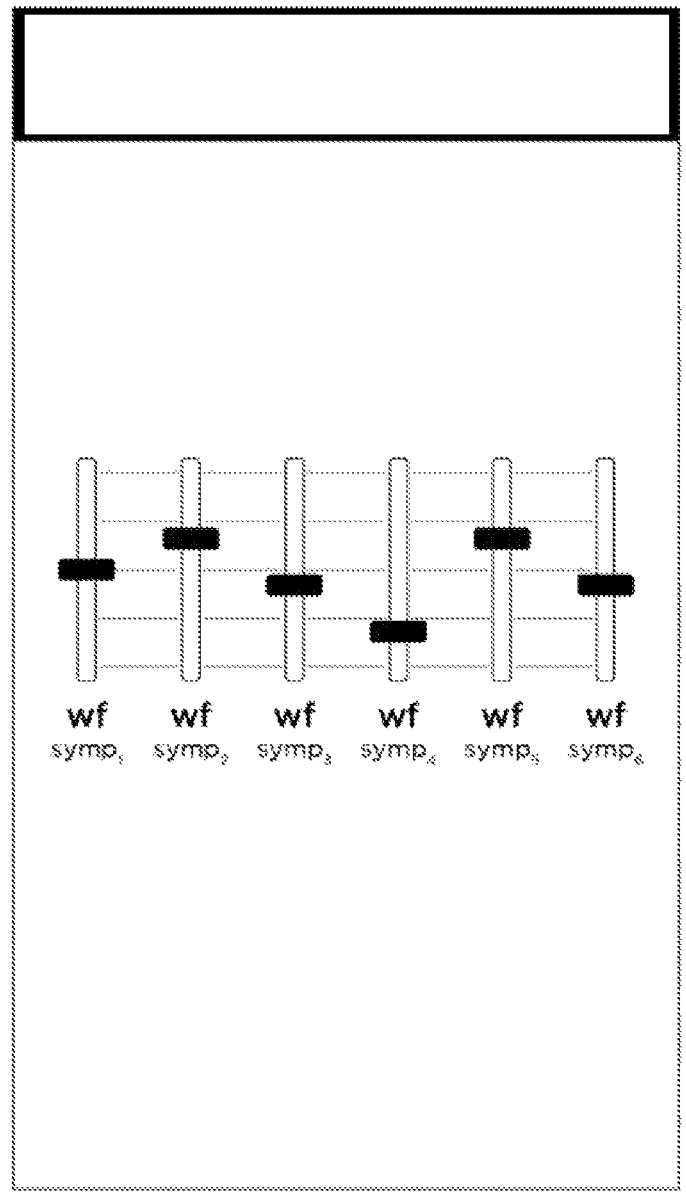

Through this invention a method requiring performance of the following tasks is therefore offered:
definition of the predetermined time for collection of the data required for calculating the CEI index,
definition of sources of reference data on the basis of an action plan,
collection of clinical data relating to oxygen measurement and spirometry tests and patients' symptoms, conversion and adjustment of the detected data using appropriate weighting factors set for example as shown in FIGS. 10 and 11. FIG. 10 shows the configuration of the value for the weighting factors for further indexes, $SpO_2$, HR, SPIROMETRY (SPIRO) and symptoms (SYMPTOMS) recorded from the patient respectively.

The CEI index is defined on the basis of the above-mentioned scores, and this is obtained by allocating a greater or lesser weight to the clinical data collected, using adjustable weighting factors (FIGS. 10 and 11).

The CEI measurement unit is a number between 0 and 100, where a higher value indicates a better condition of health, and therefore synonymous with "better efficiency" of the cardiorespiratory system.

The CEI index is calculated with contributions from the four indexes relating to $SpO_2$, heart rate (heart pulse rate), spirometry and symptoms, each of which has its own weighting factor (wf—weighting factor) (see FIG. 10) which may have a default value or alternatively may be set by the doctor.

The value of each index is calculated on the basis of the following scores:
the algorithms which will be described below;
what is established by the doctor in the action plan (or from the scientific literature) with alarm values, reference values, etc.;
the measured oxygen and spirometry values and the symptoms provided as an input by the patient using the medical application.

The formula for calculating the CEI is as follows:

$$CEI = (I_{SpO_2} \cdot wf_{SpO_2}) + (I_{HR} \cdot wf_{HR}) + (I_{SPIRO} \cdot wf_{SPIRO}) + (I_{SYMPTOMS} \cdot wf_{SYMPTOMS})$$

For the weighting factors mentioned above, the relationship $$wf_{SpO_2} + wf_{HR} + wf_{SPIRO} + wf_{SYMPTOMS} = 1$$

always applies.

If it is desired to place more importance on one of the four components or indexes in comparison with the others it is sufficient to increase the corresponding weighting factor. It is obviously possible to assign a predefined value to each weighting factor, taking care to ensure that the sum of the factors is always equal to 1.

The following indicators are then analysed:

a) The blood oxygen saturation index: $I_{SpO_2}$.

The $SpO_2$ index (obtained from the oxygen measuring test) can be calculated bearing in mind two different components represented by the partial indexes $$I_{SpO_{2_1}} \text{ and } I_{SpO_{2_2}}.$$

The partial index $$I_{SpO_{2_1}}$$

depends on the parameter $SpO_{2_{Meas}}$ (measured value) in comparison with the mean value $SpO_{2_{Avg}}$ calculated over a predetermined period of time.

The partial index $$I_{SpO_{2_2}}$$

depends on the parameter $SpO_{2_{Meas}}$ in comparison with the reference value $SpO_{2_{Ref}}$.

Let us assume that over a predetermined period of time the mean value for $SpO_2$ is 97%. This being the case, if $SpO_2$ should fall to 77% there will be a $I_{SpO_2}$ index of very close to 0, synonymous with a serious problem with the patient's health. If instead the mean $SpO_2$ value were to be 80%, then a fall in $SpO_2$ to 77% would not produce the same fall in the index.

The algorithm for analysing $SpO_2$ considers two limit values: an ideal maximum equal to 100% and a minimum threshold equal to $SpO_{2_{Thr}}$. Values of $SpO_{2_{Meas}}$ below $SpO_{2_{Thr}}$ will however produce a $I_{SpO_2}$ index of zero, synonymous with a serious problem with the patient's health.

The index is defined as follows:

$$\text{if } (SpO_{2_{Meas}} > SpO_{2_{Thr}}) \text{ then } I_{SpO_2} = 100 \cdot I_{SpO_{2_1}} \cdot I_{SpO_{2_2}}$$

$$\text{otherwise } I_{SpO_2} = 0$$

$$\text{if } (SpO_{2_{Meas}} > SpO_{2_{Avg}}) \text{ then } I_{SpO_{2_1}} = 1$$

$$\text{otherwise } I_{SpO_{2_1}} = \frac{SpO_{2_{Meas}} - SpO_{2_{Thr}}}{SpO_{2_{Avg}} - SpO_{2_{Thr}}}$$

$$\text{if } (SpO_{2_{Meas}} > SpO_{2_{Ref}}) \text{ then } I_{SpO_{2_2}} = 1$$

$$\text{otherwise } I_{SpO_{2_2}} = \frac{SpO_{2_{Meas}} - SpO_{2_{Thr}}}{SpO_{2_{Ref}} - SpO_{2_{Thr}}}$$

B) The Heart Rate Index: $I_{HR}$

The heart rate index (a parameter also obtained from the oxygen measurement test) can be calculated taking into account four different components represented by the partial indexes $I_{HR_1}$, $I_{HR_2}$, $I_{HR_3}$ and $I_{HR_4}$. Each of these components $I_{HR_X}$ is weighted with the corresponding weighting factor $wf_{HR_X}$.

The contribution of heart rate $I_{HR} \cdot wf_{HR}$ to the overall CEI index is equal by definition to:

$$(I_{HR} \cdot wf_{HR}) = \sum_{x=1}^{4} I_{HR_X} \cdot wf_{HR_X}$$

The partial index $I_{HR_1}$ depends on bradycardia.
The partial index $I_{HR_2}$ depends on tachycardia.
The partial index $I_{HR_3}$ depends on increase in heart rate within the normal range.
The partial index $I_{HR_4}$ depends on cardiac arrhythmia.
The following relationship:

$$wf_{HR} = wf_{HR_1} + wf_{HR_2} + wf_{HR_3} + wf_{HR_4}$$

where $wf_{HR}$ is the overall weighting factor for the heart rate index, always applies for the four weighting factors.

If it is wished to give more importance to one of the four components or indexes mentioned above in comparison with the others it is sufficient to increase the relative weighting factor. The invention makes it possible to assign a value for each weighting factor, taking care to ensure that the sum of all the terms is always equal to $wf_{HR}$.

The international scientific medical literature defines a normal range for heart rate which generally lies between 55 and 100 beats/minute. Below the normal range is referred to as bradycardia and above tachycardia. The further away from the normal range the more the calculated indexes fall, synonymous with the greater impact of heart rate on worsening of condition of health.

The partial index $I_{HR_1}$ is linked to bradycardia and the parameter $HR_{Meas}$ is used to calculate it.

In an actual example, the index is defined as follows:

if $HR_{Meas} \geq 55$ then $I_{HR_1}=100$ if $50 \leq HR_{Meas} < 55$ then $I_{HR_1}=80$ if $45 \leq HR_{Meas} < 50$ then $I_{HR_1}=60$ if $40 \leq HR_{Meas} < 45$ then $I_{HR_1}=40$ if $HR_{Meas} < 40$ then $I_{HR_1}=20$ These values may however be changed without altering the mechanism underlying the calculation.

The partial index $I_{HR_2}$ is linked to tachycardia and the parameter $HR_{Meas}$ is used to measure it.

The index is defined as follows:

if $HR_{Meas} \leq 100$ then $I_{HR_2}=100$ if $100 < HR_{Meas} \leq 110$ then $I_{HR_2}=80$ if $110 < HR_{Meas} \leq 120$ then $I_{HR_2}=60$ if $120 < HR_{Meas} \leq 125$ then $I_{HR_2}=40$ if $HR_{Meas} > 125$ then $I_{HR_2}=20$ These values can however be changed without altering the mechanism underlying the calculation.

The partial index $I_{HR_3}$ is linked to "heart rate" within the normal range. The calculation takes into account the possibility that the measured value $HR_{Meas}$ may exceed the mean value $HR_{Avg}$ calculated over a predetermined period of time by at least two standard deviations (SD) The index is defined as follows:

if $HR_{Meas} > (HR_{Avg} + 2 \cdot HR_{SD})$ then $I_{HR_3} = \left(\frac{HR_{Avg}}{HR_{Meas}}\right) \cdot 100$ otherwise $I_{HR_3} = 100$ Arrhythmia is a heart anomaly which gives rise to irregular sequences of heartbeats: too slow, too fast, or without linear progression.

Device 1 is able to detect an irregular heartbeat on the basis of a predetermined number of heartbeats (typically 10) and calculates the mean and standard deviation of the time intervals between the heartbeats taken into consideration.

The arrhythmia index $I_{HR_4}$ is linked to the possible presence of arrhythmia within the range 40-125 beats/minute. The index is proportional to the ratio between the standard deviation $TI_{SD}$ and the mean of the time interval $TI_{Avg}$. If the ratio between $TI_{SD}$ and $TI_{Avg}$ exceeds a predetermined threshold $TI_{ThrRatio}$ (typically 0.06) the beats are considered to be irregular.

The index is defined as follows:

if $\left(\frac{TI_{SD}}{TI_{Avg}}\right) \geq TI_{ThrRatio}$ then $I_{HR_4} = 0$ otherwise $I_{HR_4} = 100 \cdot \left(1 - \left(\frac{TI_{SD}}{TI_{ThrRatio} \cdot TI_{Avg}}\right)\right)$ c) Spirometry Index: $I_{SPIRO}$ SPIRO is the generic parameter representing spirometry and can be selected from those measured by the medical device. Among the most important of these are: PEF, FEV1, FVC, FEF25-75. Once the parameter has been selected the medical application uses it to calculate its percentage variation with respect to the reference value.

Given that the parameter $SPIRO_\%$ represents the percentage of the measured value $SPIRO_{Meas}$ with respect to the reference value $SPIRO_{Ref}$:

$$SPIRO_\% = \frac{SPIRO_{Meas}}{SPIRO_{Ref}} \cdot 100$$

The spirometry index can be calculated taking into account three different components represented by the partial indexes $I_{SPIRO_1}$, $I_{SPIRO_2}$, $I_{SPIRO_3}$:

$I_{SPIRO} = 100 \cdot I_{SPIRO_1} \cdot I_{SPIRO_2} \cdot I_{SPIRO_3}$

The partial index $I_{SPIRO_1}$ depends on SPIRO % and its mean value $SPIRO_{\% \ Avg}$.

if $(SPIRO_{\%Avg} \leq SPIRO_\%)$ then $I_{SPIRO_1} = 1$ if $(SPIRO_\% < 10)$ then $I_{SPIRO_1} = 0$ otherwise $I_{SPIRO_1} = \frac{SPIRO_\% - 10}{(SPIRO_{\%Avg} - 10)}$ The partial index $I_{SPIRO_2}$ depends on $SPIRO_\%$ and the predetermined upper limit of the reference value which is 100%.

if $(SPIRO_\% \geq 100)$ then $I_{SPIRO_2} = 1$ if $(SPIRO_\% < 10)$ then $I_{SPIRO_2} = 0$ otherwise $I_{SPIRO_2} = \frac{SPIRO_\% - 10}{(100 - 10)}$ It will be noted that 10 and 100 are the minimum and maximum values of $SPIRO_\%$ respectively.

The partial index $I_{SPIRO_3}$ depends on the daily variability in the spirometry parameter over a predetermined period of time. Daily variability is an indicator of the functioning of the airways.

The index $I_{SPIRO_3}$ depends on the so-called "variability" in the spirometry parameter with respect to the minimum measured value $SPIRO_{Min}$ and the maximum measured value $SPIRO_{Max}$ recorded over a predetermined period of time.

In practice, when the variability threshold $SPIRO_{Thrvar}$ indicated in the plan of action specified by the doctor (typically 20%) is exceeded, then there is a greater risk of exacerbation. In this case the index $I_{SPIRO_3}$ produces a fall in the spirometry index $I_{SPIRO}$ which in turn brings about a fall in the value of the overall CEI index to indicate a worsening in condition of health.

The partial index linked to the variability in the spirometry parameter is defined as follows:

$$\text{if } \left(\frac{SPIRO_{Max} - SPIRO_{Min}}{SPIRO_{Max}}\right) \cdot 100 > SPIRO_{ThrVar} \text{ then}$$

$$I_{SPIRO_3} = \frac{SPIRO_{Min}}{SPIRO_{Max}} \text{ otherwise } I_{SPIRO_3} = 1$$

The reference value is based on the anthropometric data for the patient and can be found from tables or calculated using formulae published by the main international organisations operating in the field of respiratory diseases. Alternatively the reference values can be defined by considering the patient's better typical values.

d) Symptoms Index: $I_{SYMPTOMS}$

The symptoms index depends on the value of the scores for individual symptoms.

For simplicity of description we can by way of example restrict the analysis (but not in any limiting way) to six symptoms which are generally sufficient for the self-management of respiratory diseases. Obviously the symptoms may also be fewer in number.

| Description | Score | Index | Weighting factor |
| --- | --- | --- | --- |
| Shortness of breath | $score_{symp_1}$ | $I_{symp_1}$ | $wf_{symp_1}$ |
| Coughing | $score_{symp_2}$ | $I_{symp_2}$ | $wf_{symp_2}$ |
| Absence of breath | $score_{symp_3}$ | $I_{symp_3}$ | $wf_{symp_3}$ |
| Cardiac oppression | $score_{symp_4}$ | $I_{symp_4}$ | $wf_{symp_4}$ |
| Production of catarrh | $score_{symp_5}$ | $I_{symp_5}$ | $wf_{symp_5}$ |
| Heartburn | $score_{symp_6}$ | $I_{symp_6}$ | $wf_{symp_6}$ |

The term $I_{SYMPTOMS} \cdot wf_{SYMPTOMS}$ of the CEI formula is by definition equal to $$I_{SYMPTOMS} \cdot wf_{SYMPTOMS} = \sum_{x=1}^{6} I_{symp_x} \cdot wf_{symp_x}$$

The following relationship applies between the symptom weighting factors:

$$wf_{SYMPTOMS} = wf_{symp_1} + wf_{symp_2} + wf_{symp_3} + wf_{symp_4} + wf_{symp_5} + wf_{symp_6}$$

If it is desired to give more importance to one symptom in comparison with the others it is sufficient to change the corresponding weighting factor as for example indicated in FIG. 11. The invention makes it possible to assign a value to each weighting factor, making sure to check that the sum of all the terms is always equal to $wf_{SYMPTOMS}$.

Each of the six symptoms will be assessed by the patient with a score, for example from 0 to 3, assigned on the basis of presence and level of severity: 0=symptom absent; 1=mild symptom; 2=moderate symptom; 3=severe symptom (the scale from 0 to 3 is purely indicative).

The partial indexes for symptoms are calculated using the following formula (with x identifying the symptom considered where 3 identifies the maximum score assigned to each symptom):

$$I_{symp_x} = 100 \cdot \frac{3 - score_{symp_x}}{3}$$

As indicated, the CEI index refers to the patient's condition of health and variations in that condition. Assessment of quantitative objectives provides important indications which can give significant answers to improve condition of health, thus initiating a virtuous cycle. In fact the results of the current assessment become the basis for planning subsequent improvement.

The index introduced by the present invention can be seen as a value which is representative of the efficiency of the cardiorespiratory system over a certain period of time; this in turn represents a general model of health which is particularly suitable for patients suffering from respiratory diseases.

The CEI index can be used to monitor patients' state of health on a daily basis, so as to help them self-manage their disease and improve their state of health. Use of this index is useful to patients, health sector professionals and other interested parties.

The purpose of the CEI index is to establish a consistent approach for measuring the health condition of patients and variations in that condition. This index can be used as a tool for primary monitoring to ensure that the condition of health of patients suffering from respiratory diseases achieves the expected results.

The aim of the CEI index as an operating indicator is to help patients to assess changes in cardiorespiratory performance. In addition to this, the index is also intended to provide an example of a method of calculation which might be used as an objective approach to monitor the efficacy of treatment administered to a patient.

According to the action plan provided by the doctor, it is therefore possible to establish a suitable period of time for monitoring a patient, based on spirometry and oxygen measurement tests performed using device 1. A mean for the data used to calculate the CEI index can then be established over a predetermined period of time using the following technique. Over a number of days (for example 28 days or four weeks) the first element of the mean is obtained by taking the mean of a subset, equal to the first set of a number of days (for example the first seven days or the first week). The subset is then changed "moving the period forward", that is excluding the first day of the first subset (for example the first day of week one) and including the first day following the first subset (for example the eighth day or the first day of the second week). This new second subset will provide the second element of the current mean. This process continues until the entire period of interest is covered.

Thanks to the invention there is a system comprising a medical device capable of interacting, through BLE chips, with a medical application present in comparison means such as a microprocessor unit or a client or a remote web server, the medical device receives a request for the transmission of physiological data (in digital form) relating to oxygen measurement and spirometry tests performed by a patient through using device 1 (and stored in the memory unit in control unit 13) from the medical application and sends digital data pertinent to the operating state of the device.

The medical application processes the digital physiological data, compares them with corresponding restored reference values available in the action plan provided by the treating doctor, integrates them with the "score" provided by the patient for his own systems and, as a final result, provides a cardiorespiratory efficiency index (CEI) relating to the patient's condition of health. The application method, based on data managed by the doctor, suggests actions which are to be taken in accordance with reference values and alarm levels originally configured in accordance with what the doctor himself has prescribed in the patient's digital action plan.

It is known that the device can perform an oxygen measurement and a spirometry measurement simultaneously with sending data to the web or before the request for delivery of such data from the abovementioned application. Placing a finger on photometric touch sensor 7 of portable medical device 1 and simultaneously breathing into component 3 (comprising the flow measurement device) thus make it possible to make both oxygen and spirometry measurements.

The invention has been demonstrated and described using the solutions preferred for it; it will be clear to those skilled in the art that various changes may be made to the form and detail of the invention without thereby going beyond the spirit and the field of application of the invention.

For example, the web-based medical application may easily be replaced by an application directly installed on a client—which could be a smartphone or a tablet—without any need for a browser or a nearby internet network or any other connection. Such "local" application is however updated via the internet by the application present on the web managed by the doctor who has the patient's action plan.

Another example of a different embodiment of the proposed invention, which might be used in the light of any structural changes made without going beyond the scope of the invention, is different representations of the CEI index value and its variations.

In addition to numerical display from 0 to 100, this index may be displayed by an intuitive image which expresses conditions of health and possible variations in them, such as for example a tree or a plant in a flower vase. In the case of deterioration the state of health expressed by the CEI index value could effectively be represented by fallen leaves or flowers which bend or wilt. Conversely, if health improves, there could be new leaves or new flowers, or leaves which grow and flowers which flower.

Another type of representation of the CEI index value could be an archery target where an arrow at the centre represents an optimum condition of health, while the further the arrow is from the centre the worse the patient's health will be.

Even these variants fall within the scope of the following claims.

The invention claimed is:

1. A system for monitoring the state of health of a patient suffering from a respiratory disease comprising:
   a portable medical device (1) having a body (2) that is elongated in a first direction with an upper surface (9) and an opposite lower surface (17) that extend in the first direction,
   i) a tubular element for detecting respiratory flow (5a) located at a first end of the body and protruding from the upper surface (9) and aligned with an air exit on the lower surface (17), a flow measuring device (3) configured for performing a spirometry measurement, the flow measuring device (3) being comprised of a turbine (5) inserted in and connected to the tubular element (5a), the turbine (5) being sensitive to respiratory flow, the turbine (5) being caused to rotate by the air expelled forcefully by a patient performing a spirometry test,
   wherein the body (2) of the portable medical device (1) is a hand-held size that allows performing the spirometry measurement by being held and operated by one hand of a user,
   ii) an oxygen measuring sensor (4) configured for performing a measurement of blood oxygen saturation and heart rate, wherein the oxygen measuring sensor (4) is comprised of a recessed seat (8) located on upper surface (9) of the body (2), a reflecting photometric touch sensor (7) located in the recessed seat (8) on upper surface (9) of the body (2), positioning a finger on a top of the photometric touch sensor (7) obtains a reading of signals linked to an oxygen measurement, and
   iii) a control unit (13) that simultaneously measures the patient's spirometry and oxygen measurement parameters through the flow measuring device (3) and the oxygen measuring sensor (4), the control unit (13) being located within the body remote from the flow measuring device (3), the control unit (13) including a bluetooth communications chip, the bluetooth communications chip being a BLE (Bluetooth Low Energy) chip,
   wherein the portable medical device (1) is free of any display that displays the patient's spirometry and oxygen measurement parameters; and
   a computing device wirelessly bluetooth connectable to the portable medical device (1), the computing device comprising a storage device operatively connected to a processor unit running an application configured for making comparisons and monitoring the patient's health using a personalised action plan for the patient provided by a doctor caring for the patient,
   said processor unit being configured for comparing the oxygen measurements and/or the spirometry measurements with corresponding values in the personalised action plan stored in the storage device,
   said computing device being separate from said medical device (1) and being connected wirelessly thereto,
   wherein the portable medical device (1) is configured to transmit, using the bluetooth communications chip, the oxygen measurements and the spirometry measurements to the computing device; and
   a display (100, 101, 102, 103, 104; 200, 201, 202; 90, 91, 92, 93) separate from the portable medical device (1) and operatively connected to the computing device, the display being configured for showing results of said comparison between the oxygen measurements and/or the spirometry measurements and corresponding values in the patient's personalised action plan, said results defining the patient's state of health and identifying possible exacerbation of the disease.

2. The system according to claim 1, wherein said recessed seat (8) has an internal or back wall (10) in which the photometric touch sensor (7) is located connected to the upper surface (9) of the body (2) by a wall (8a).

3. The system according to claim 1, wherein said computing device includes the display (100, 101, 102, 103, 104; 200, 201, 202; 90, 91, 92, 93).

4. The system according to claim 3, wherein,
   said computing device is a smartphone, a tablet or a computer or other fixed or mobile digital device.

5. The system according to claim 3, wherein said application running on said processor unit is configured for making the comparisons and includes an algorithm monitoring and checking said spirometry and oxygen measurements and configured for providing a cardiorespiratory efficiency index or CEI indicating a patient's state of health, said index being then displayed on the display.

6. The system according to claim 5, wherein said CEI index is a number and depends on the spirometry and oxygen measurement data made using the portable medical device (1), and subjective data provided by the patient device relating to the intensity of symptoms of the disease according to that patient's perception of severity found from corresponding values in the personalised action plan provided by the treating doctor.

7. The system according to claim 6, wherein said CEI index depends on a value relating to the patient's blood oxygen saturation and heart rate, these data being obtained from the oxygen measurement.

8. The system according to claim 5, wherein the CEI index is defined by the following formula $$CEI = (I_{SpO_2} \cdot wf_{SpO_2}) + (I_{HR} \cdot wf_{HR}) + (I_{SPIRO} \cdot wf_{SPIRO}) + (I_{SYMPTOMS} \cdot wf_{SYMPTOMS})$$

where $I_{SpO_2}$=is the blood oxygen saturation index;
$I_{HR}$=is the heart rate index;
$I_{SPIRO}$=is the spirometry index;
$I_{SYMPTOMS}$=is the index which depends on an assessment of the intensity of individual symptoms experienced by the patient;
$wf_{SpO_2}$, $wf_{HR}$, $wf_{SPIRO}$, $wf_{SYMPTOMS}$=are weighting or importance factors which are to be given to individual indexes, the sum of all these factors being equal to 1,
said index $I_{SpO_3}$ depends on a measured saturation value, the mean saturation value calculated over a predetermined period of time and the reference value;
said index $I_{HR}$ depends on at least one of possible bradycardia, tachycardia, cardiac arrhythmia and normal heartbeat in a range of 50-100 beats per minute;
said index $I_{SPIRO}$ depending on at least one of the following parameters PEF, FEV1, FVC, FEF25-75.

9. A method for monitoring the health of a patient suffering from respiratory airways disease, said method being implemented using the system according to claim 1 and providing for the performance of a spirometry and/or oxygen measurement by the patient, said measurements being made with a single medical device, the method comprising:
a) storing the personalised action plan managed by a doctor caring for said patient in the storage device of the computing device separately from said portable medical device,
b) sending the spirometry and/or oxygen measurements made to the computing device, said computing device comparing said measured values with corresponding oxygen and spirometry values set in the personalised action plan stored in said storage device,
c) making said measurement of the spirometry and/or oxygen values being by holding said portable medical device in a single hand, the oxygen measurement being obtained through contact between the hand and the portable medical device, and
d) displaying the results of the comparison made by said computing device on the display, said display of the results showing the patient's state of health and any exacerbation of the disease.

10. The method according to claim 9, wherein the dispatch of spirometry and/or oxygen values to the computing device takes place alternatively while oxygen and spirometry measurements are being made or on request by said computing device to said portable medical device.

11. The method according to claim 9, wherein said computing device is one of i) a web server hosting the application, the storage device being located on the web server, and ii) a smartphone, a tablet or a computer or other fixed or mobile digital device.

12. The method according to claim 9, wherein the results of the comparison are defined by means of a Cardiorespiratory Efficiency Index or CEI index which indicates the patient's state of health and suggests actions which should be taken in accordance with what is established in the personalised action plan provided by the treating doctor.

13. The method according to claim 9, wherein said treating doctor continuously updates the personalised action plan on the basis of oxygen measurement and/or spirometry values measured using the portable medical device.

14. The method according to claim 9, wherein the oxygen and spirometry measurements which are made simultaneously by the patient who holds the portable medical device in a single hand, said patient placing a finger on the reflecting touch sensor (7) and simultaneously blowing into the turbine (5).

15. The method according to claim 12, further comprising:
defining a predetermined time to perform the spirometry measurement and/or the oxygen measurement necessary for calculating the CEI index;
defining corresponding reference values present in the personalised action plan;
recording spirometry and oxygen measurement values obtained;
recording of data relating to the intensity of symptoms by the patient, comparing the reference values and the measured values to define the CEI index; and
displaying that index.

16. The method according to claim 12, wherein provision is made for graphically representing the CEI index on the display.

17. The system of claim 1, wherein the recessed seat is of an elongated shape so as to fit the anatomy of any adult or child patient.

18. The system of claim 1, wherein,
the computing device comprises a web server hosting the application and including the storage device,
wherein the display is operatively connected to the application hosted on the web server, and
wherein the web server is reachable via the internet by the treating doctor in order to keep the patient's personalised action plan up to date.

19. The system according to claim 1, wherein said computing device is a smartphone, a tablet or a computer or other fixed or mobile digital device configured for Bluetooth low energy connection to the portable medical device.

* * * * *